United States Patent
Hashiguchi et al.

(10) Patent No.: US 6,887,200 B2
(45) Date of Patent: *May 3, 2005

(54) METHOD OF SUPPORTING HEALTH CHECKUP, AN APPARATUS FOR IMPLEMENTING THE SAME AND A MEDIUM RECORDING THEIR PROCESSING PROGRAMS

(75) Inventors: Takeshi Hashiguchi, Tokyo-to (JP); Hiroshi Takeuchi, Matsudo (JP); Hitoshi Matsuo, Musashino (JP); Kiyoteru Noguchi, Tokyo-to (JP); Kazuyuki Shimada, Kawaguchi (JP)

(73) Assignee: Hitachi, Ltd., Tokyo (JP)

( * ) Notice: Subject to any disclaimer, the term of this patent is extended or adjusted under 35 U.S.C. 154(b) by 68 days.

This patent is subject to a terminal disclaimer.

(21) Appl. No.: 10/406,505

(22) Filed: Apr. 4, 2003

(65) Prior Publication Data

US 2003/0167188 A1 Sep. 4, 2003

Related U.S. Application Data

(63) Continuation of application No. 09/493,078, filed on Jan. 28, 2000, now Pat. No. 6,547,727.

(30) Foreign Application Priority Data

Mar. 17, 1999 (JP) .......................................... P11-71332

(51) Int. Cl.[7] .......................... A61B 5/00; A61B 10/00; G06F 17/60; G06K 9/62

(52) U.S. Cl. ...................... 600/300; 128/920; 128/923; 705/3

(58) Field of Search ............................... 600/300–301, 600/309, 345–347, 365; 128/904, 920–925; 705/2–4, 9; 706/16, 21–22, 25

(56) References Cited

U.S. PATENT DOCUMENTS

| | | | |
|---|---|---|---|
| 5,935,060 A | * | 8/1999 | Iliff ............................ 600/300 |
| 6,246,975 B1 | | 6/2001 | Rivonelli et al. |
| 6,248,063 B1 | | 6/2001 | Barnhill et al. |
| 6,269,339 B1 | | 7/2001 | Silver |
| 6,547,727 B1 | * | 4/2003 | Hashiguchi et al. ........ 600/300 |

* cited by examiner

Primary Examiner—Max F. Hindenburg
Assistant Examiner—Michael Astorino
(74) Attorney, Agent, or Firm—Antonelli, Terry, Stout & Kraus, LLP

(57) ABSTRACT

A health checkup supporting method, apparatus and computer readable recording medium for predicting a checkup receiver's risk of suffering from a disease. The method and apparatus include inputting checkup receiver information indicating information showing the possibility of affecting the incidence of a disease obtained with respect to a checkup receiver who has received a health checkup, and finding a value of a risk of the checkup receiver's suffering from the disease based on the inputted checkup receiver information and risk parameters obtained from a ratio of the past checkup receivers' suffering from the disease. The checkup receiver information includes results of at least one of a clinical examination and results of a genetic examination conducted with respect to the checkup receiver.

15 Claims, 9 Drawing Sheets

FIG.3

| Checkup Receiver ID | Date of Data Entry | Results of Clinical Examination | | | Results of Question-and-Answer Examination | | | | Results of Genetic Examination | | | |
|---|---|---|---|---|---|---|---|---|---|---|---|---|
| | | Fasting Blood Glucose Value | Glucose Tolerance Test | Glycuresis | ... | Q1 | Q2 | Q3 | ... | NIDDM1 | NIDDM2 | NIDDM3 | ... |
| 106 | 99/02/26 | 1 | 2 | 4 | | ○ | | ○ | | ○ | | | |

Interview sheet

Q1. Do you have your skin itching?

Q2. Are you liable to have botching and not quick to have it recovered?

Q3. Do you feel that your eyesight is weakening?
(Do you need to wear glasses or do you need to get glasses adjusted?)

Q4. Not neuralgia nor rheumatic, do you tend to have your legs aching and free from it after a short rest?

| Items to Be Checked at Clinical Examination for Diabetes | | | | Risk Parameter p1 |
|---|---|---|---|---|
| Fasting Blood Glucose Value | Glucose Tolerance Test | Glycuresis | ... | |
| 1 | 1 | 1 | | 0.20 |
| 1 | 1 | 2 | | 0.23 |
| 1 | 1 | 3 | | 0.25 |
| 1 | 1 | 4 | | 0.30 |
| 1 | 2 | 1 | | 0.21 |
| 1 | 2 | 2 | | 0.24 |
| 1 | 2 | 3 | | 0.27 |
| 1 | 2 | 4 | | 0.31 |

| Question-and-Answer Items for Diabetes | | | | Risk Parameter p2 |
|---|---|---|---|---|
| Q1 | Q2 | Q3 | ... | |
| | | | | 0.20 |
| | ○ | | | 0.23 |
| | | ○ | | 0.25 |
| | ○ | ○ | | 0.30 |
| ○ | | | | 0.21 |
| ○ | ○ | | | 0.24 |
| ○ | | ○ | | 0.27 |
| ○ | ○ | ○ | | 0.31 |

| Diabetes-Related Genes | | | | Risk Parameter p3 |
|---|---|---|---|---|
| NIDDM1 | NIDDM2 | NIDDM3 | ... | |
|  |  |  |  | 0.30 |
|  | ○ |  |  | 0.33 |
|  |  | ○ |  | 0.35 |
|  | ○ | ○ |  | 0.40 |
| ○ |  |  |  | 0.31 |
| ○ | ○ |  |  | 0.34 |
| ○ |  | ○ |  | 0.37 |
| ○ | ○ | ○ |  | 0.41 |

FIG.8

| Checkup Receiver ID (801) | Date of Data Entry (802) | Results of Clinical Examination (803) ||| | Results of Question-and-Answer Examination (804) ||| | Results of Genetic Examination (805) |||| | History of Diseases (806) |
|---|---|---|---|---|---|---|---|---|---|---|---|---|---|
| | | Fasting Blood Glucose Value | Glucose Tolerance Test | Glycuresis | ... | Q1 | Q2 | Q3 | ... | NIDDM1 | NIDDM2 | NIDDM3 | ... | |
| 101 | 99/02/16 | 1 | 1 | 1 | | | | | | | | | | |
| 102 | 99/02/17 | 1 | 2 | 4 | | ○ | | | | ○ | ○ | | | Incidence of Diabetes |
| 103 | 99/02/19 | 1 | 1 | 2 | | ○ | | | | | | | | |
| 104 | 99/02/21 | 1 | 2 | 1 | | ○ | | ○ | | | | | | |
| 105 | 99/02/22 | 1 | 2 | 3 | | ○ | ○ | ○ | | ○ | ○ | | | |
| 106 | 99/02/26 | 1 | 2 | 4 | | | | ○ | | | | | | |
| .. | | | | | | | | | | | | | | |

# METHOD OF SUPPORTING HEALTH CHECKUP, AN APPARATUS FOR IMPLEMENTING THE SAME AND A MEDIUM RECORDING THEIR PROCESSING PROGRAMS

CROSS REFERENCE TO RELATED APPLICATION

This is a continuation of U.S. application Ser. No. 09/493,078, filed Jan. 28, 2000, now issued as U.S. Pat. No. 6,547,727, the subject matter of which is incorporated by reference herein.

BACKGROUND OF THE INVENTION

The present invention relates to a health checkup system to diagnose the health status of a checkup receiver, more particularly a technique effectively applicable to a health checkup system to predict the risk of the checkup receiver's suffering a disease based on results of a clinical examination, a question-and-answer examination and a genetic examination combined.

When a healthy person wishes to know the status of his health or predict how much risk of suffering a certain disease he is possibly exposed to while he continues his habitual life-style, it is general to receive a health checkup.

In a conventional health checkup, the health status of a health checkup receiver is examined through a clinical examination and a question-and-answer examination and the health status of the checkup receiver is diagnosed with the results of these examinations compared with the average results obtained from healthy persons. Receiving such a health checkup, a person can roughly know the possibility of developing a certain disease and utilize its result as a guidance to improve his habitual daily life.

In recent years, meanwhile, there has been increasingly conducted a genetic examination detecting gene mutation in a sample such as blood. A medical examination of this kind is only applicable to diseases with cause genes determined. Despite this, the above-described examination is advantageous to make a precritical diagnosis possible. Therefore, this examination is often conducted as a prenatal checkup to diagnose gene-caused diseases with the mutation of specific genes known as their causes.

Incidentally, a system of predicting the life-time incidence of Alzheimer's disease, capable of accurately obtaining data constituting a basis for the judgment of an early examination and treatment of Alzheimer's disease, is disclosed in Japanese Patent Laid-Open No. Hei 10-261029.

The above-described conventional health checkup to diagnose the health status of a checkup receiver by comparing the results of a clinical examination and a question-and-answer examination with their average values makes it hard to conduct a diagnosis incorporating personal differences.

The above genetic examination is conducted with the checkup receiver's personal genetic difference taken into account. However, it is difficult to diagnose by only the genetic examination as it is not applicable to diseases with cause genes not determined or diseases depending on various cause genes and environmental factors.

SUMMARY OF THE INVENTION

In view of the above, the present invention has its object to resolve the above problems and provide a technique to enhance the precision of the calculation of a value of a health checkup receiver's risk to a disease.

According to the present invention, a check receiver's risk of suffering from a disease is predicted based on the results of a clinical examination, the results of a question-and-answer examination and the results of a genetic examination combined in the health checkup system predicting a risk of incidence of a disease of a checkup receiver who has received a health checkup.

According to the present invention, the results of a clinical examination indicating the bio-information of a checkup receiver, the results of a question-and-answer examination indicating information including the habitual activities of the checkup receiver and the results of a genetic examination indicating the genetic characteristics of the checkup receiver as an individual are inputted as the checkup receiver information indicating information showing the possibilities of affecting the incidence of a disease obtained with respect to the checkup receiver who has received a health checkup.

By comparing the inputted checkup receiver information with risk parameters obtained from a disease incidence ratio calculated for other persons in the past, a risk value of the possible incidence of a disease is found and diagnostic messages and remedial measures are indicated in correspondence with the obtained risk value.

According to the present invention as described above, since the results of a genetic examination showing the genetic characteristics of a checkup receiver are used for a diagnosis in addition to the results of a clinical examination indicating the bio-information of the checkup receiver and the results of the question-and-answer examination including the checkup receiver's habitual activities, it is possible to diagnose the checkup receiver's liability to a life-dependent disease together with a life-style and genetic characteristics, making such a diagnosis matching the characteristics of a health checkup receiver.

Since environmental factors such as life habits and the results of a genetic examination are diagnosed together, it is possible to diagnose a disease which cannot be diagnosed only through an examination of cause genes, widening the range of diseases it can diagnose.

As described above, the health checkup system according to the present invention conducts a risk prediction of a disease of a checkup receiver based on the results of a genetic examination indicating the genetic characteristics of an individual together with the results of a clinical examination and a question-and-answer examination, the precision of the calculation of a risk value with respect to a health checkup receiver can be enhanced.

BRIEF DESCRIPTION OF THE DRAWINGS

FIG. 3 is a table showing an example of a checkup receiver information according to the present invention;

FIG. 4 is a table showing an example of a question-and-answer examination according to the present invention;

FIG. 5 is a table showing an example of a clinical examination result parameter table 107 according to the present invention;

FIG. 6 is a table showing an example of a question-and-answer examination result parameter table 108 according to the present invention;

FIG. 8 is a table showing an example of a checkup receiver information database 207 according to the present invention;

DETAILED DESCRIPTION OF PREFERRED EMBODIMENTS

Now, there will be explained a health checkup system embodying the present invention to predict a checkup receiver's risk of suffering from a disease.

Figure 1:
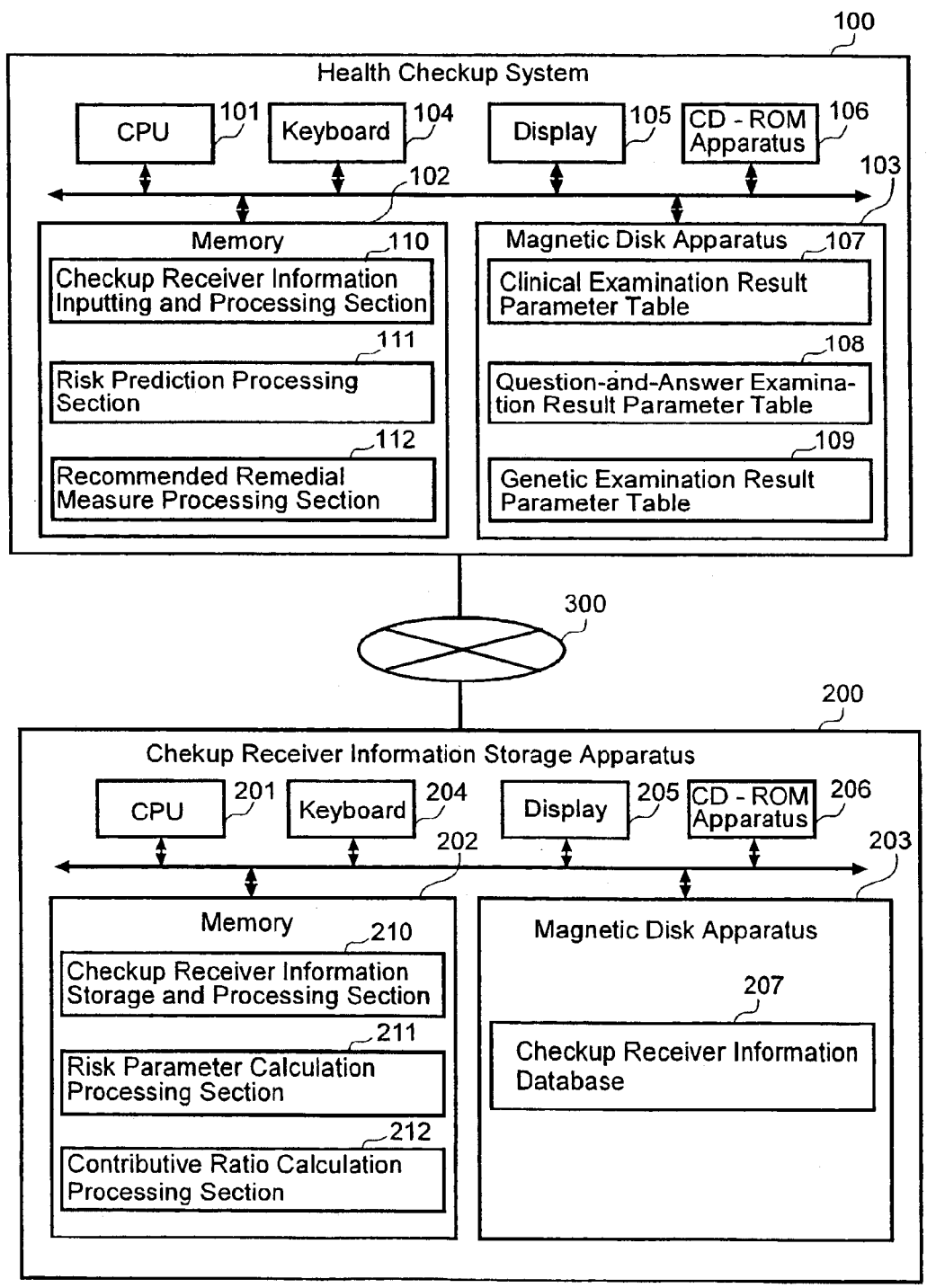
FIG. 1 is a diagram showing a schematic configuration of a health checkup system according to the present invention.

FIG. 1 is a diagram showing a schematic configuration of a health checkup system according to the present invention. As shown in FIG. 1, a health checkup apparatus 100 in an embodiment according to the present invention comprises CPU 101, a memory 102, a magnetic disk apparatus 103, a keyboard 104, a display 105, a CD-ROM apparatus 106, a clinical examination result parameter table 107, a question-and-answer result parameter table 108 and a genetic examination result parameter table 109.

CPU 101 is a control device to control the whole operations of the health check apparatus 100. The memory 102 is a memory device to load various programs to control the whole operations of the health checkup system 100 and data. The magnetic disk apparatus 103 is a memory device to store the above processing programs and data.

The keyboard 104 is an input device to conduct input operations such as the designation of a disease with respect to which a risk value is calculated. The display 105 is an output device to indicate diagnostic messages, including the result of a risk value calculated, and remedial measures, among other things.

The CD-ROM apparatus 106 is a device to read CD-ROM storing the above-described processing programs and data. The clinical examination result parameter table 107 is a table storing risk parameters corresponding to the results of clinical examinations conducted in the past.

The question-and-answer examination result parameter table 108 is a table storing risk parameters corresponding to the results of question-and-answer examinations conducted in the past. The genetic examination result parameter table 109 is a table storing risk parameters corresponding to the results of genetic examinations conducted in the past.

The health checkup apparatus 100 has a checkup receiver information inputting and processing section 110, a risk prediction processing section 111 and a recommended remedial measure presenting and processing section 112.

The checkup receiver information inputting and processing section 110 is a processing section to input a checkup receiver information indicating information showing disease-incidence possibility of the checkup receiver obtained with respect to the checkup receiver who has received a health checkup. The risk prediction processing section 111 is a processing section to calculate the risk value of the checkup receiver's possibly suffering from a disease based on the inputted checkup receiver information and risk parameters for the incidence of a disease obtained from health checkup receivers in the past. The recommended remedial measure presenting and processing section 112 is a processing section to show a remedial measure to lower the above-described risk value if it is higher than a predetermined value.

A program to make the health checkup apparatus 100 function as the checkup receiver information inputting and processing section 110, the risk prediction processing section 111 and the remedial measure presenting and processing section 112 is first recorded on such a medium as CD-ROM and loaded into the memory for its execution. A medium recording the program may be anything other than CD-ROM.

A checkup receiver information storage apparatus 200 is composed of CPU 201, a memory 202, a magnetic disk appararus 203, a keyboard 204, a display 205, a CD-ROM apparatus 206 and a checkup receiver information database 207.

CPU 201 is a control apparatus to control the whole operations of the checkup receiver information storage apparatus 200. The memory 202 is a memory apparatus to load various programs for controlling the whole operations of the checkup receiver information storage apparatus 200 and data.

The magnetic disk apparatus 203 is a memory apparatus to store the above processing programs and data. The keyboard 204 is an input apparatus to instruct and execute the calculation of risk parameters and their contributive ratios. The display 205 an output apparatus to indicate the results of processing of risk parameters and their contributive ratios.

The CD-ROM apparatus 206 is a device to read CD-ROM storing the processing programs and data described above. The checkup receiver information database 207 is a database to store information obtained from a health checkup receiver at the time of the health checkup and patient information obtained from outpatients visiting a hospital after incidence of a disease.

The checkup receiver information storage apparatus 200 has a checkup receiver information storage and processing section 210, a risk parameter calculation processing section 211 and a contributive ratio calculation processing section 212.

The checkup receiver information storage and processing apparatus 210 is a processing section to store in the checkup receiver information database 207 the checkup receiver information obtained at the time of a health checkup and information obtained from outpatients visiting a hospital after the incidence of a disease. The risk parameter calculation processing section 211 is a processing section to calculate the risk parameters. The contributive ratio calculation processing section 212 is a processing section to calculate the contributive ratio of each risk parameter in order to work out the above risk value.

A program to make the checkup receiver information storage apparatus 200 function as the checkup receiver information storage and processing apparatus 210, the risk parameter calculation processing section 211 and the contributive ratio calculation processing section 212 is first recorded on such a medium as CD-ROM and then loaded into the memory for its execution. A medium recording the program may be anything other than CD-ROM.

As shown in FIG. 1, the health checkup apparatus 100 in this embodiment of the present invention is connected to the checkup receiver information storage apparatus 200 through a network 300, so that a checkup receiver information inputted into the health checkup apparatus 100 is fed to the checkup receiver information storage apparatus 200 through the network 300. In this embodiment of the present invention, only the single health checkup apparatus 100 is connected to the checkup receiver information storage apparatus 200. The checkup receiver information storage system 200 may totally manage all checkup receiver information obtained from a plurality of health checkup apparatuses 100 connected to the checkup receiver information storage apparatus 200 through the network 300.

Figure 2:
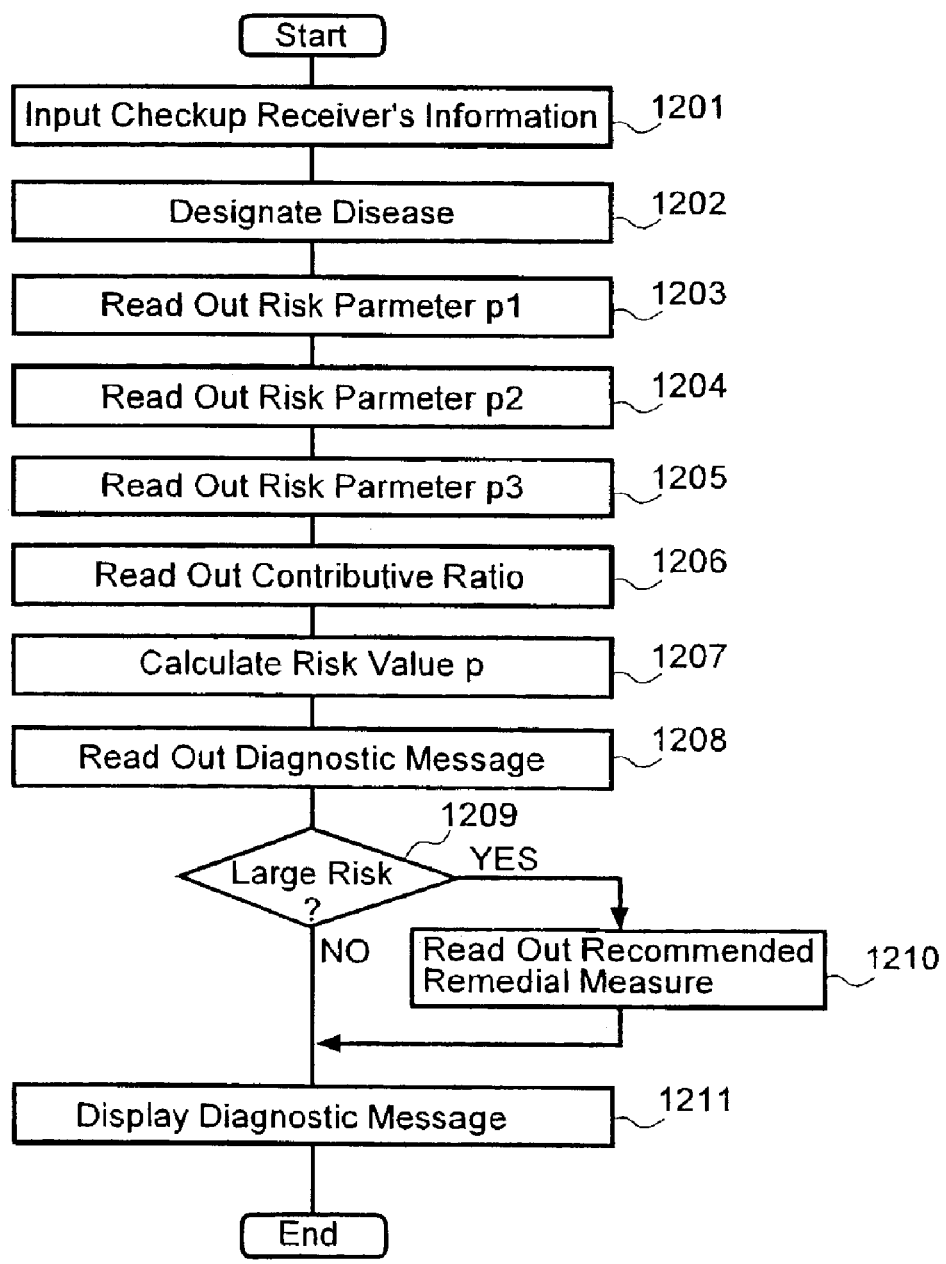
FIG. 2 is a flowchart indicting steps of risk predicting processing according to the present invention.

FIG. 2 is a flowchart showing steps of risk prediction processing according to the present invention. In Step 1201, the checkup receiver information inputting and processing section 110 of the health checkup apparatus 100 receives in the results of a clinical examination, the results of a question-and-answer examination and the results of a genetic examination as a checkup receiver information.

FIG. 3 is a table showing an example of a checkup receiver information according to the present invention. As shown in FIG. 3, a checkup receiver information in this embodiment of the present invention includes a checkup receiver ID301, a data entry date 302, the results of a clinical examination 303, the results of a question-and-answer examination 304 and the results of a genetic examination 305.

The checkup receiver ID301 is an identification number to identify a specific checkup receiver. The data entry date 302 includes a year, a month and a date when the checkup receiver information is inputted. The results of a clinical examination 303 are data indicating the bio-information of the checkup receiver obtained through various examinations.

The results of a question-and-answer examination 304 are checkup receiver-related data including the daily habits and other aspects of the checkup receiver obtained through an entry into an interview sheet. The results of a genetic examination 305 include information indicating the genetic characteristics of a checkup receiver and show data indicating whether the genes of the checkup receiver has gene mutation associated with the incidence of any disease.

FIG. 3 shows an example of diabetes-related checkup receiver information. In the results of a clinical examination 303 according to the present invention, a fasting blood glucose value and values shown in a glucose tolerance test and glycuresis have numerical indications designating a specific range of values. For example, the fasting glucose value of the checkup receiver is in the range of a glucose value represented by numeral 1. It should be noted that when this value is larger an actually measured value corresponding to it as shown in the results of the corresponding clinical examination 303 is larger.

An encircled mark in the results of a question-and-answer examination 304 indicates that the checkup receiver answered "yes" to a question "Q1," etc. in an interview sheet and a blank box in the results of the question-and-answer examination 304 indicates a "no" answer. "NIDDM1" in the results of a genetic examination 305 shows a gene associated with incidence of non-insulin dependent diabetes, with a circle indicating that the checkup receiver has its gene mutation and a blank indicating the absence of such gene mutation.

FIG. 4 is a table showing an example of a question-and-answer examination according to the present invention. Shown in FIG. 4 is an interview sheet used for a diagnosis of diabetes. This daily-taken calories and habitual activities such as regular exercises may be added.

Then in Step 1202 shown in FIG. 2, the risk prediction processing section 111 accepts the designation of a disease subject to a risk prediction. In Step 1203, risk parameters p1 corresponding the results of a checkup receiver's clinical examination 303 are read from the clinical examination result parameter table 107.

FIG. 5 is a table showing an example of the clinical examination result parameter table 107 according to the present invention. As shown in FIG. 5, the clinical examination result parameter table 107 represents the probability of suffering from diabetes within a specific period as a risk parameter p1 for checkup receivers associated with the clinical examination results. Out of checkup receivers with fasting blood glucose, a glucose tolerance test and glycuresis showing values "1", "2" and "4" respectively, 31 percent are shown to suffer from diabetes within a specific period. A fasting blood glucose value and values indicated by fasting blood glucose, a glucose tolerance test and glycuresis as shown in the clinical test result parameter table 107 have numerical indications specifying a cope of specific values for each item as shown in FIG. 3.

In Step 1204, a risk parameter p2 corresponding to the results of a question-and-answer examination 304 of a checkup receiver as shown in FIG. 3 is read from the question-and-answer examination result parameter table 108.

FIG. 6 is a table showing an example of the question-and-answer examination result parameter table 108. The question-and-answer examination result parameter table 108 as shown in FIG. 6 represents the probability of suffering from diabetes within a specific period as a risk parameter p2 for checkup receivers associated with the question-and-answer examination results. Like in FIG. 3, incidentally, a circle to a question such as Q1 in the interview sheet is "yes" to that question and a blank means "no."

In Step 1205, a risk parameter p3 corresponding to the results of a genetic examination 305 of a checkup receiver as shown in FIG. 3 is read from the genetic examination result parameter table 109.

Figure 7:
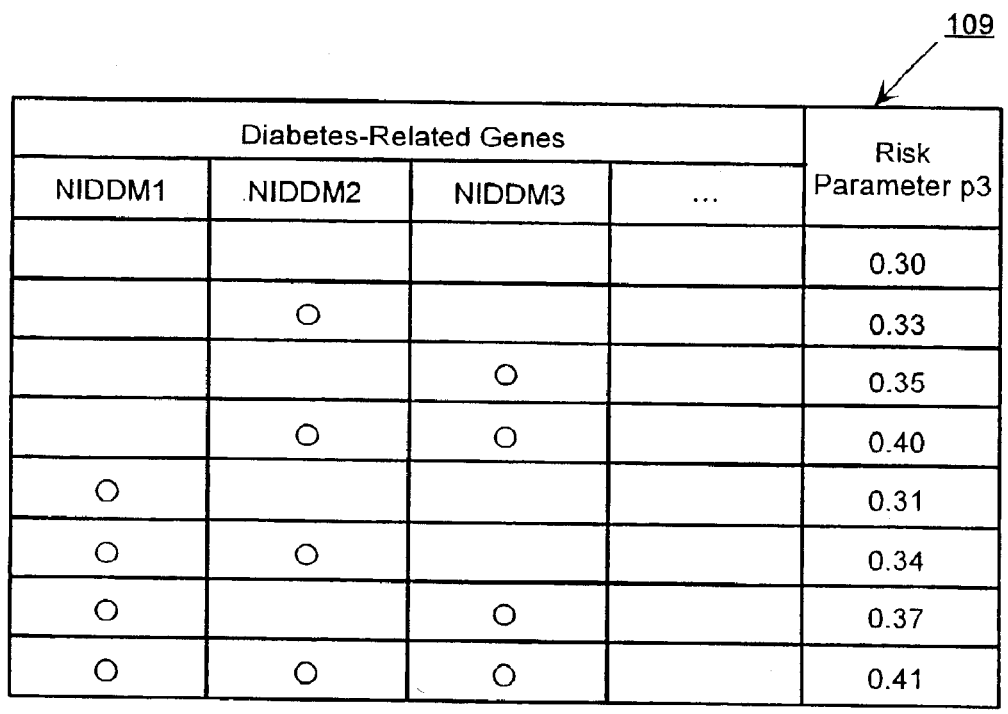
FIG. 7 is a table showing an example of a genetic examination result parameter table 109 according to the present invention.

FIG. 7 is a table showing an example of the genetic examination result parameter table 109. As shown in FIG. 7, the genetic examination result parameter table 109 represents the probability of suffering from diabetes within a specific period as a parameter p3 for checkup receivers associated with the genetic examination results. Like in FIG. 3, each mark added to diabetes-related gene "NIDDM1," shows a gene associated with incidence of non-insulin dependent diabetes mellitus (NIDDM), with a circle indicating that a checkup receiver has gene mutation and a blank indicating that a checkup receiver has no gene mutation.

In Step 1206, parameters each showing a contributive ratio to the risk value of each risk parameter a, b or c is read out and, in Step 1207, a risk value P is calculated through the following formula.

$$P = a \cdot p1 + b \cdot p2 + c \cdot p3 \qquad \text{(Equation 1)}$$

The equation 1 shows an example of formulas used to calculate a risk value in Step 1207. P is a risk value showing the probability of a checkup receiver's suffering from a disease within a specific period; p1 a risk parameter showing the probability of disease incidence within a specific period calculated based on the results of the past clinical examinations; p2 a risk parameter showing the probability of disease incidence within a specific period as calculated based on the results of the past question-and-answer examination; and p3 a risk parameter showing the probability of disease incidence within a specific period as calculated based on the results of the past genetic examinations.

Meanwhile, a is the contributive ratio of the results of a clinical examination contributing to a general risk with respect to the specific disease, b is the contributive ratio of the results of a question-and-answer examination contributing to the general risk with respect to the specific disease and c is the contributive ratio of the results of a genetic examination contributing to the general risk with respect to the specific disease, their relationship being shown as a+b+c=1.

In Step 1208, a diagnostic message corresponding to the risk value P calculated as above is read out. In Step 1209, it is verified whether or not the above calculated risk value P is higher than the predetermined level and, if it is, remedial measures are read out from the recommended remedial measure presenting processing section 112 in Step 1210.

In Step 1211, a diagnostic message corresponding to the risk value P calculated as above is displayed and remedial measures are presented if they are read out in Step 1210.

For example, when the calculated risk value P is low, a message like "Your probability of the incidence of diabetes is less than P %. You don't pay any special attention in your daily life." is displayed.

When the calculated risk value P is high, a diagnostic message like "Your values of diabetes-related items subject to the clinical examination are high and, judged together with genetic factors, your probability of the incidence of diabetes is P %. You need to change your habitual activities and you are recommended to receive a detailed health checkup every six months." is displayed. As remedial measures, the recommended remedial measure processing section 112, after its processing, displays a daily total calorie intake urging a calorie intake limitation and aerobics exercise to consume fats in Step 1210.

These diagnostic messages and remedial measures are set beforehand for applicable risk values P and values of items applicable to a checkup receiver information.

As described above, in addition to the results of a clinical examination 303 indicating the bio-information of the checkup receiver and the results of a question-and-answer examination 304 including information showing the habitual activities, etc. of a checkup receiver, the embodiment of the present invention uses the results of a genetic examination 305 indicting the genetic characteristics of the checkup receiver for a diagnosis, so that it is possible to diagnose a checkup receiver's liabilities to a life-dependent disease, etc. together with habitual activities and genetic characteristics, making such a diagnosis matching the characteristics of the checkup receiver.

Since a diagnosis is conducted based environmental factors such as habitual activities and the results of a genetic examination combined in this embodiment of the present invention, it is made possible to diagnose a disease which could not be diagnosed only through a genetic examination and to widen a scope of diagnosable diseases.

After the above diagnostic messages and recommended remedial measures are displayed, the risk predicting processing section 111 completes its processing by the sending the inputted check receiver information to the checkup receiver information storage apparatus 200. The checkup receiver information storage and processing section 210 of the checkup receiver information storage apparatus 200 stores in the checkup receiver information database 207 the checkup receiver information at the time of a health checkup or a patient's information at the time of disease incidence transmitted as explained above.

FIG. 8 is a table showing an example of the checkup receiver information database 207 according to the present invention. As shown in FIG. 8, the checkup receiver information database 207 according to the present invention includes a checkup receiver ID 801, the date of a data entry (802, the results of a clinical examination 803, the results of a question-and-answer examination 804, the results of a genetic examination 805 and a history of diseases 806.

The checkup receiver ID 801 is an identification number to identify a checkup receiver. The date of a data entry 802 includes a year, a month and a date when the checkup receiver information was inputted. The results of a clinical examination 803 are data showing the bio-information of the checkup receiver obtained through various examinations.

The results of a question-and-answer examination 804 are the checkup receiver-related data, including information on the habitual activities, etc. of the checkup receiver obtained through an entry into an interview sheet. The results of a genetic examination 805 including information indicating the genetic characteristics of the checkup receiver are data on the genes of the checkup receiver diseases-causing gene mutation. The history of diseases 806 lists up the names of diseases the checkup receiver has suffered from in the past.

As shown in FIG. 8, the checkup receiver information database 207 stores the history of diseases 806 of a checkup receiver together with the checkup receiver information as shown in FIG. 3. The information accumulated in the checkup receiver information database 207 is used for the calculation of the above-described risk parameters and their contributing ratios.

Figure 9:
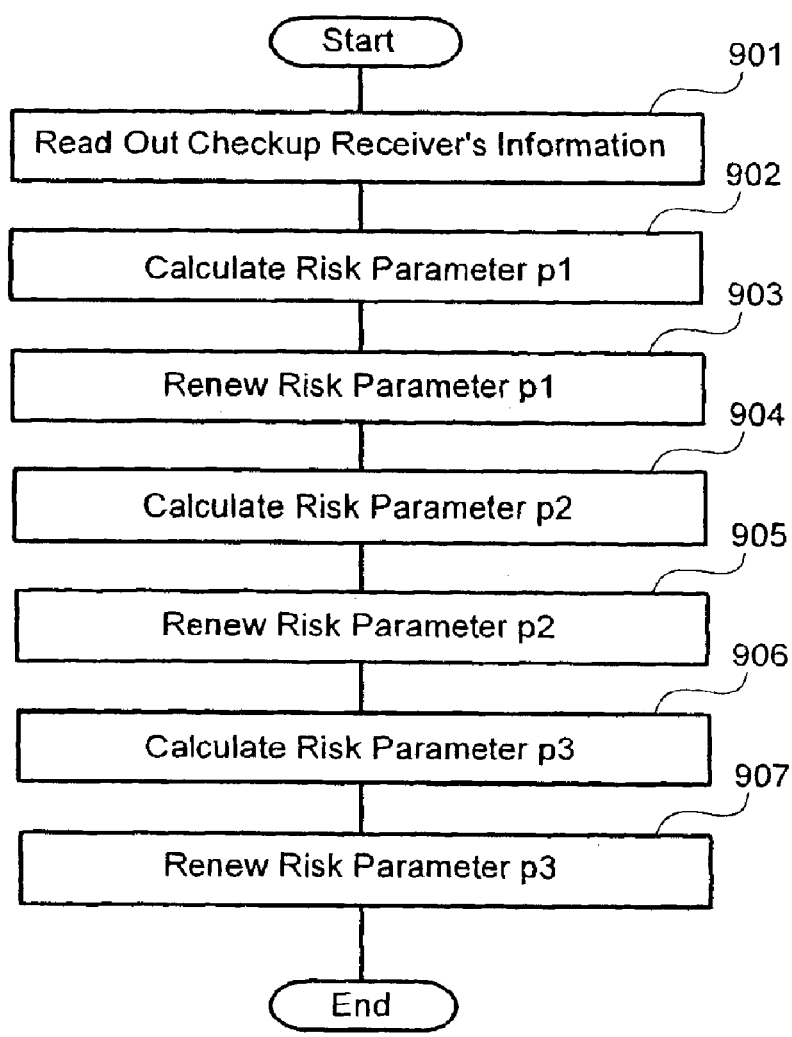
FIG. 9 is a flowchart showing steps of risk parameter calculation processing according to the present invention.

FIG. 9 is a flowchart showing steps of risk parameter calculation processing. The risk parameter calculation processing section 211 of the checkup receiver information storage apparatus 200 starts its operation when specific conditions are satisfied like the checkup receiver information database 207 is renewed or a predetermined period elapses from the previous calculation processing. In Step 901, it reads out from the checkup receiver information database 207 the checkup receiver information over a predetermined period.

In Step 902, checkup receivers corresponding to each other in the clinical examination 803 out of the above read-out checkup receiver information are counted, with reference to the history of diseases 806 out of the checkup receiver information the ratio of checkup receivers' suffering from a specific disease among the checkup receivers is calculated every disease, and a risk parameter p1 for each disease is found.

In Step 903, the risk parameter p1 obtained as described above is sent to the health checkup apparatus 100. The health checkup apparatus 100 stores the received risk parameter p1 in the clinical examination result parameter table 107.

In Step 904, checkup receivers corresponding to each other in the question-and-answer examination 804 out of the above read-out checkup receiver information are counted, with reference to the history of diseases 806 out of the checkup receiver information the ratio of checkup receiver' suffering from a specific disease among the checkup receivers is calculated every disease, and a risk parameter p2 for each disease is found.

In Step 905, the risk parameter p2 worked out as described above is sent to the health checkup apparatus 100. The health checkup apparatus 100 stores the received risk parameter p2 into the question-and-answer result parameter table 108.

In Step 906, checkup receivers corresponding to each other in the genetic examination results 805 out of the above read-out checkup receiver information are counted and, with reference to the history of diseases 806, the ratio of checkup receiver's suffering from a specific disease among the checkup receivers is calculated every disease and a risk parameter 3 for each disease is found.

In step 907, the risk parameter p3 worked out as described above is sent to the health checkup apparatus 100. The health checkup apparatus 100 stores the received risk parameter p3 in the genetic examination result parameter table 109.

Figure 10:
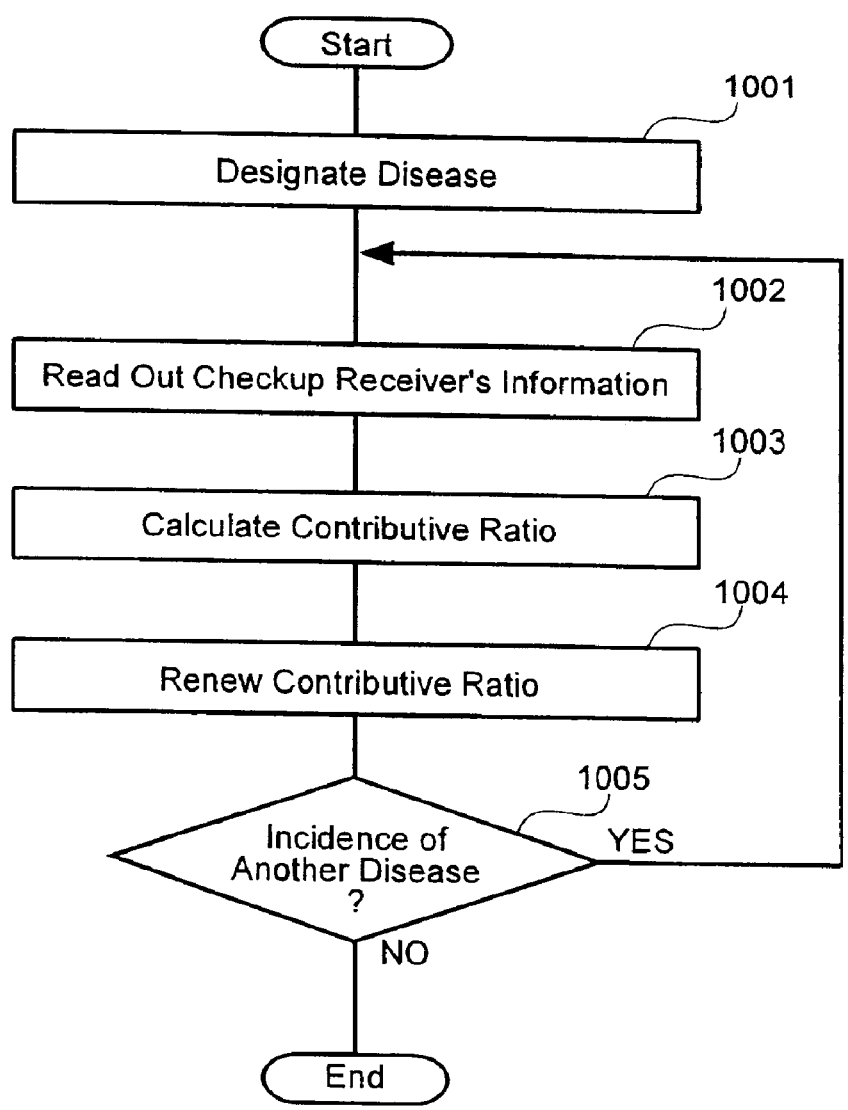
FIG. 10 is a flowchart showing steps of contributive ratio calculation processing according to the present invention.

FIG. 10 is a flowchart showing steps of the contributive ratio calculation processing according to the present invention. Like the risk parameter calculation processing section 211, the contributive ratio calculation processing section 212 of the checkup receiver information storage apparatus 200 starts its operation when specific conditions are satisfied like the checkup receiver information database 207 is renewed or a predetermined period elapses from the previous calculation processing. In Step 1001, a disease to calculate its contributive ratio first is selected and set out of the history of disease 806 in the checkup receiver information database 207.

The checkup receiver information of the checkup receiver's suffering from the designated disease is read out from the checkup receiver information database 207 in Step 1002, relationships between the results of a clinical examination 803, the results of a question-and-answer examination 804 and the results of a genetic examination 805 for the read-out checkup receiver information and, the designated disease are studied, and contributive ratios a, b and c weighted in accordance with the strength of their relationships are calculated.

With dispersions obtained for objective items of the results of a clinical examination 803, the results of a question-and-answer examination 804 and the results of a genetic examination 805 for the read-out checkup receiver information, for example, a, b and c as contributive ratios in proportion to their reciprocals are calculated. In this embodiment of the present invention, a contributive ratio is calculated for each item of the results of a clinical examination 803, the results of a question-and-answer examination 804 and the results of a genetic examination 805. In a case where objective items for such contributive ratio calculation processing are diversifying and a number of items not specifically relating to the incidence of the designated disease are included, a contributive ratio for each item is used to calculate the risk value P by utilizing a contributive ratio calculated for each objective item.

In Step 1004, the contributive ratio obtained as described above is sent to the health checkup apparatus 100. The health checkup apparatus 100 stores the received contributive ratio as the contributive ratios a, b and c to calculate the risk value P of the disease.

In Step 1005, a disease is searched through the history of disease 806 of the checkup receiver information database 207. It is also checked whether there is a disease for which a contributive ratio has not been calculated and, if there is, the processing returns to Step 1002 with the name of that disease designated. When contributive ratios are calculated for all the diseases stored in the history of diseases 806 of the checkup receiver information database 207, this processing is completed and finished.

As described above, this embodiment of the present invention sends a checkup receiver information inputted from the health checkup apparatus 100 to the checkup receiver information storage apparatus 200 to calculate risk parameters and their contributive ratios at the checkup receiver information storage apparatus 200 and feed them back to the health checkup apparatus 100, so that it is possible to heighten the precise calculation of risk values as checkup receiver information is accumulated.

According to the health checkup system embodying the present invention as described above, the prediction of a check receiver's risk liability to a disease is conducted with the results of a genetic examination indicating the genetic characteristics of an individual added to the results of a clinical system and the results of a question-and-answer examination, making it possible to enhance the precision of the calculation of a checkup receiver's disease-incidence risk value.

According to the present invention, the health checkup system conducts a risk prediction of a disease of a checkup receiver based on the results of a genetic examination indicating the genetic characteristics of an individual together with the results of a clinical examination and a question-and-answer examination, the precision of the calculation of a risk value with respect to a health checkup receiver can be enhanced.

What is claimed is:

1. A health checkup supporting method for predicting a checkup receiver's risk of suffering from a disease, said method comprising the steps of:

inputting checkup receiver information indicating information showing the possibility of affecting the incidence of a disease obtained with respect to a checkup receiver who has received a health checkup;

finding a value of a risk of the checkup receiver's suffering from the disease based on inputted checkup receiver information, risk parameters obtained from a ratio of past checkup receiver information suffering from the disease, and a contributive ratio to each said risk parameters; and wherein said checkup receiver information includes results of a clinical examination and a genetic examination conducted with respect to the checkup receiver.

2. A health checkup supporting method as claimed in claim 1, further comprising a step of presenting remedial measures recommended to lower the risk value when said risk value is higher than a predetermined level.

3. A health checkup supporting method as claimed in claim 2, wherein the results of the clinical examination are results of a physical testing of the checkup receiver, and the results of the genetic examination are results of a gene based testing of the checkup receiver.

4. A health checkup supporting method as claimed in claim 1, wherein the results of the clinical examination are results of a physical testing of the checkup receiver, and the results of the genetic examination are results of a gene based testing of the checkup receiver.

5. A health checkup supporting method as claimed in claim 1, wherein the finding of the value of a risk of the checkup receiver's suffering from the disease is at least one of a determined percentage value and a relationship with respect to a percentage value.

6. A health checkup supporting apparatus for predicting a checkup receiver's risk of suffering from a disease, said apparatus comprising:

a checkup receiver information inputting and processing section for inputting checkup receiver information indicating information showing the possibility of affecting the incidence of a disease obtained with respect to a checkup receiver who has received a health checkup;

a risk prediction calculation section for finding a value of a risk of the checkup receiver's suffering from the disease based on inputted checkup receiver information, risk parameters obtained from a ratio of past checkup receiver information suffering from the disease, and a contributive ratio to each said risk parameters; and wherein said checkup receiver information includes results of a clinical examination and a genetic examination conducted with respect to the checkup receiver.

7. A health checkup supporting apparatus as claimed in claim 6, further comprising a remedial measures presenting and processing section for presenting remedial measures recommended to lower the risk value when said risk value is higher than a predetermined level.

8. A health checkup supporting apparatus as claimed in claim 7, wherein the results of the clinical examination are results of a physical testing of the checkup receiver, and the results of the genetic examination are results of a gene based testing of the checkup receiver.

9. A health checkup supporting apparatus as claimed in claim 6, wherein the results of the clinical examination are results of a physical testing of the checkup receiver, and the results of the genetic examination are results of a gene based testing of the checkup receiver.

10. A health checkup supporting apparatus as claimed in claim 6, wherein said risk prediction calculation section determines the value of a risk of the checkup receiver's suffering from the disease in terms of at least one of a determined percentage value and a relationship with respect to a percentage value.

11. A computer readable recording medium storing a program enabling a computer to function as a health checkup apparatus for predicting a checkup receiver's risk of suffering from a disease said computer readable recording medium comprising:

a checkup receiver information inputting and processing section for inputting checkup receiver information indicating information showing the possibility of affecting the incidence of a disease obtained with respect to a checkup receiver who has received a health checkup;

a risk prediction processing section for finding a value of a risk of the checkup receiver's suffering from a disease based on inputted checkup receiver information, risk parameters obtained from a ratio of past checkup receiver information suffering from the disease, and a contributive ratio to each said risk parameters; and wherein said checkup receiver information includes results of a clinical examination and a genetic examination conducted with respect to the checkup receiver.

12. A computer readable recording medium as claimed in claim 11, further comprising a remedial measures presenting and processing section for presenting remedial measures recommended to lower the risk value when said risk value is higher than a predetermined level.

13. A computer readable recording medium as claimed in claim 12, wherein the results of the clinical examination are results of a physical testing of the checkup receiver, and the results of the genetic examination are results of a gene based testing of the checkup receiver.

14. A computer readable recording medium as claimed in claim 11, wherein the results of the clinical examination are results of a physical testing of the checkup receiver, and the results of the genetic examination are results of a gene based testing of the checkup receiver.

15. A computer readable recording medium as claimed in claim 11, wherein said risk prediction calculation section determines the value of a risk of the checkup receiver's suffering from the disease in terms of at least one of a determined percentage value and a relationship with respect to a percentage value.

* * * * *